US006027877A

United States Patent [19]
Wagner, Jr.

[11] Patent Number: 6,027,877
[45] Date of Patent: Feb. 22, 2000

[54] USE OF IMMOBILIZED MISMATCH BINDING PROTEIN FOR DETECTION OF MUTATIONS AND POLYMORPHISMS, PURIFICATION OF AMPLIFIED DNA SAMPLES AND ALLELE IDENTIFICATION

[75] Inventor: Robert E. Wagner, Jr., Vermontville, N.Y.

[73] Assignee: Gene Check, Inc., Vermontville, N.Y.

[21] Appl. No.: 08/147,785

[22] Filed: Nov. 4, 1993

[51] Int. Cl.$^7$ .......................... C12Q 1/68; G01N 33/543
[52] U.S. Cl. ................ 435/6; 435/7.5; 436/518; 436/528; 436/529; 436/530; 436/531; 935/77; 935/78
[58] Field of Search ................ 435/6, 7.5, 975; 436/510, 528, 529, 530, 531, 536, 501; 530/413; 935/77, 78

[56] References Cited

U.S. PATENT DOCUMENTS 5,459,039 10/1995 Modrich et al. ..................... 435/6

FOREIGN PATENT DOCUMENTS

93/02216  2/1993  WIPO .
93/22457  11/1993  WIPO .

OTHER PUBLICATIONS

Bowen, B. et al., "The Detection of DNA–Binding Proteins by Protein Blotting", *Nucl. Acids Res.* 8:1–20 (1979).
Miskimins, W.K. et al., "Use of a Protein–Blotting Procedure and a Specific DNA Probe to Identify Nuclear Proteins that Recognize the Promoter Region of the Transferrin Receptor Gene", *Proc. Natl. Acad. Sci. USA* 82:6741–6744 (1985).
Keller, A.D. et al., "Selection of Sequences Recognized by a DNA Binding Protein Using a Preparative Southwestern Blot", *Nucl. Acids Res.* 19:4675–80 (1991).
Norby, P.L. et al., "Determination of Recognition–Sequences for DNA–Binding Proteins by a Polymerase Chain Reaction Assisted Binding Site Selection Method (BSS) Using Nitrocellulose Immobilized DNA Binding Protein", *Nucl. Acids Res.* 20:6317–6321.
Singh et al., "Molecular Cloning of an Enhancer Binding Protein: Isolation by Screening of an Expression Library with a Recognition Site DNA", *Cell* 52:415–423 (1988); Singh et al., *BioTechniques* 7:253–261 (1989).
Vinson et al., "In Situ Detection of Sequence–Specific DNA Binding Activity Specified by a Recombinant Bacteriophage", *Genes & Devel.* 2:801–806 (1988).
Oliphant, A.R. et al., "Defining the Sequence Specificity of DNA–Binding Proteins by Selecting Binding Sites from Random–Sequence Oligonucleotides: Analysis of Yeast GCN4 Protein", *Molec. Cell. Biol.* 9:2944–2949 (1989).
Perrino, F.W. et al., "Interaction of a Folded Chromosome–Associated Protein With Single–Stranded DNA–Binding Protein of *Escherichia coli*, Identified by Affinity Chromatography", *J. Biol. Chem.* 263:11833–11839 (1988).

Meyer, R.R. et al., "The Single–Stranded DNA–Binding Protein of *Escherichia coli*", *Microbiol. Rev.* 54:342–380 (1990).
Myers, R.M. et al., "Recent Advances in the Development of Methods for Detecting Single–base Substitutions Associated with Human Genetic Diseases", *Cold Spring Harbor Symp. Quant. Biol.* 51:275–284 (1986).
Gibbs, R. et al., "Identification and Localization of Mutations at the Lesch–Nyhan Locus by Ribonuclease A Cleavage", *Science* 236:303–305 (1987).
Lu, A.S. et al., "Detection of Single DNA Base Mutations with Mismatch Repair Enzymes", *Genomics* 14:249–255 (1992).
Cotton, R.G. et al., "Reactivity of cytosine and thymine in single–base–pair mismatches with hydroxylamine and osmium tetroxide and its application to the study of mutations", *Proc. Natl. Acad. Sci. USA* 85:4397–4401 (1988).
Cotton, R.G., "Chemical reactivity of matched cytosine and thymine bases near mismatched and unmatched bases in a heteroduplex between DNA strands with multiple differences", *Nuc. Acids Res* 17:4223–4233 (1989).
Grompe, M. et al., "Scanning detection of mutations in human ornithine transcarbamoylase by chemical mismatch cleavage", *Proc. Natl. Acad. Sci. USA* 86:5888–5892 (1989).
Radman, M. et al., "Mismatch Repair in *Escherichia coli*", *Annu. Rev. Genet.* 20:523–538 (1986).
Radman, M. et al., "The High Fidelity of DNA Duplication", *Sci. Amer.*, Aug. 1988, pp. 40–46.
Modrich, P., "Methyl–directed DNA Mismatch Correction", *J. Biol. Chem.* 264:6597–6600 (1989).
Lahue, R.S. et al., "DNA Mismatch Correction in a Defined System", *Science* 245:160–164 (1989).
Jiricny, J. et al., "Mismatch–containing oligonucleotide duplexes bound by the *E. coli* mutS–encoded Protein", *Nucl. Acids Res.* 16:7843–7853 (1988).
Su, S.S. et al., "Mispair Specificity of Methyl–directed DNA Mismatch Correction in Vitro", *J. Biol. Chem.* 263:6829–6835 (1988).
Lahue, R.S. et al., "Methyl–directed DNA mismatch repair in *Escherichia coli*", *Mutat. Res.* 198:37–43 (1988).

(List continued on next page.)

*Primary Examiner*—W. Gary Jones
*Assistant Examiner*—Debra Shoemaker
*Attorney, Agent, or Firm*—Morrison & Foerster LLP

[57] ABSTRACT

A method for detecting mutations, such as a single base change or an addition or deletion of about one to four base pairs, is based on the use of an immobilized DNA mismatch–binding protein, such as MutS, which binds to a nucleic acid hybrid having a single base mismatch or unpaired base or bases, thereby allowing the detection of mutations involving as little as one base change in a nucleotide sequence. Such a method is useful for diagnosing a variety of important disease states or susceptibilities, detecting the presence of a mutated oncogene and for isolating or removing by affinity chromatography duplex DNA molecules containing mismatches such as error–containing molecules in PCR–amplified DNA samples. Also provided are kits useful for practicing the methods of the present invention.

16 Claims, 1 Drawing Sheet

OTHER PUBLICATIONS

Dohet, C. et al., "Large non–homology in heteroduplex DNA is processed differently than single base pair mismatches", *Mol. Gen. Genet.* 206:181–184 (1987).

Jones, M. et al., "Repair of a Mismatch Is Influenced by the Base Composition of the Surrounding Nucleotide Sequence", *Genetics* 115:605–610 (1987).

Lu, A.L. et al., "Repair of Single Base–Pair Transversion Mismatches of *Escherichia coli* in Vitro: Correction of Certain A/G Mismatches Is Independent of dam Methylation and Host mutHLS Gene Functions", *Genetics* 118:593–600 (1988).

Haber L.T. et al., "Nucleotide Sequence of the *Salmonella typhimurium* mutS Gene Required for Mismatch Repair: Homology of MutS and HexA of *Streptococcus pneumoniae*", *J. Bacteriol.* 170:197–202 (1988).

Pang, P.P. et al., "Identification and Characterization of the mutL and mutS Gene Products of *Salmonella typhimurium* LT2", *J. Bacteriol* 163:1007–1015 (1985).

Priebe S.D. et al., "Nucleotide Sequence of the hexA Gene for DNA Mismatch Repair in *Streptococcus pneumoniae* and Homology of hexA to mutS of *Escherichia coli* and *Salmonella typhimurium*", *J. Bacteriol.* 170:190–196 (1988).

Valle G. et al., "The Sequence of a 6•3 kb Segment of Yeast Chromosome III Reveals an Open Reading Frame Coding for a Putative Mismatch Binding Protein", 1991 *Yeast* 7:981–988.

Miret J.J. et al., "Characterization of a DNA Mismatch–binding Activity in Yeast Extracts", 1993, *J. Biol. Chem.* 268:3507–3513.

Stephenson, C. et al., "Selective Binding to DNA Base Pair Mismatches by Proteins from Human Cells", 1989, *J. Biol. Chem.* 264:21177–21782.

Karran, P. et al., "Mismatch binding proteins and tolerance to alkylating agents in human cells", 1990, *Mutat. Res.* 236:269–275.

Hughes M.J. et al., "The Purification of a Human Mismatch–binding Protein and Identification of Its Associated ATPase and Helicase Activities", 1992, *J. Biol. Chem.* 267:23876–23882.

Reenan, A.G. et al., "Isolation and Characterization of Two Saccharomyces cerevisiae Genes Encoding Homologs of the Bacterial HexA and MutS Mismatch Repair Proteins", 1993, *Genetics* 132:963–973.

Reenan, A.G. et al., "Characterization of Insertion Mutations in the *Saccharomyces cerevisiae* MSH1 and MSH2 Genes: Evidence for Separate Mitochondrial and Nuclear Functions", 1993, *Genetics* 132:975–985.

Shimada, T. et al., "A 165–Base Pair Sequence Between the Dihydrofolate Reductase Gene and the Divergently Transcribed Upstream Gene Is Sufficient for Bidirectional Transcriptional Activity", *J. Biol. Chem.* 264:20171 (1989).

Linton, J. et al., "Dual Bidirectional Promoters at the Mouse dhfr Locus: Cloning and Characteriztaion of Two mRNA Classes of the Divergently Transcribed Rep–1 Gene", *Molec. Cell. Biol.* 7:3058–3072 (1989).

Fujii, H. et al., "Isolation and Characterization of cDNA Clones Derived from the Divergently Transcribed Gene in the Region Upstream from the Human Dihydrofolate Reductase Gene", *J. Biol. Chem.* 264:10057 (1989).

Butler, 1992. "The behavior of antigens and antibodies immobilized on a solid plane", *Structure of Antigens* (Van Regenmortel, ed.) CRC Press, Boca Raton, pp. 209–259.

Butler et al, 1992. The physical and functional behavior of capture antibodies adsorbed on polystyrene. J. Immunol. Meth. 150:77–90.

Butler, et al, 1993. The immunochemistry of sandwich ELISAs–VI. Greater than 90% of monoclonal and 75% of polyclonal anti–fluoresyl capture antibodies (CABS) are denatured by passive adsorption. Mol. Immunol. 30:1165–1175.

Parker et al, Mar. 1992. Repair of DNA heteroduplexes containing small heterdogenes sequences in *Escherichia coli*. PNAS 89:1730–34.

Towbin et al, 1984. Immunoblotting and dot immunobinding—current status and outlook. J Immunol. Meth. 72:313–340.

Lew et al, 1993. Affinity selection of polymerase chain reaction products by DNA–binding proteins. Meth Enzymol. 218:526–534.

Seed, 1982. "Attachment of nucleic acids to nitrocellulose and diagnosis—substituted supports", in *Genetic Engineering*. vol. 4 (J.K. Setlow et al, eds.) Plenum Press, N.Y. pp. 91–102.

Lishanskaya et al, Oct. 1992, Mutation detection in the cystic fibrosis gene using an *E. coli* mismatch binding protein, mutS. Am J Human Genet 51 (4 suppl.): A385. Abstract #1517.

Saiki et al, 1989. Genetic analysis of amplified DNA . . . Proc Natl Acad Sci (USA) 86:6230–6234.

us, for example,
assay sensitivity can be increased through the use of detect-
ably labeled reagents, wherein the labels may be enzymes
(Kourilsky et al., U.S. Pat. No. 4,581,333), radioisotopes
(Falkow et al., U.S. Pat. No. 4,358,535; Berninger, U.S. Pat.
No. 4,446,237), fluorescent labels (Albarella et al., EP
144914), chemical labels (Sheldon III et al., U.S. Pat. No.
4,582,789; Albarella et al., U.S. Pat. No. 4,563,417), modi-
fied bases (Miyoshi et al., EP 119448), and the like.# USE OF IMMOBILIZED MISMATCH BINDING PROTEIN FOR DETECTION OF MUTATIONS AND POLYMORPHISMS, PURIFICATION OF AMPLIFIED DNA SAMPLES AND ALLELE IDENTIFICATION

BACKGROUND OF THE INVENTION

1. Field of the Invention

The invention in the fields of molecular biology and medicine relates to a method for detecting mutations involving as little as one base change or a single base addition to, or deletion from, the wild-type DNA sequence, as well as methods for removing mismatch-containing DNA from batches of amplified DNA.

2. Description of the Background Art

Progress in human molecular and medical genetics depends on the efficient and accurate detection of mutations and sequence polymorphisms, the vast majority of which results from single base substitutions and small additions or deletions. Assays capable of detecting the presence of a particular mutation or mutant nucleic acid sequence in a sample are therefore of substantial importance in the pre- diction and diagnosis of disease, forensic medicine, epide- miology and public health. Such assays can be used, for example, to detect the presence of a mutant gene in an individual, allowing determination of the probability that the individual will suffer from a genetic disease. The ability to detect a mutation has taken on increasing importance in early detection of cancer or discovery of susceptibility to cancer with the discovery that discrete mutations in cellular oncogenes can result in activation of that oncogene leading to the transformation of that cell into a cancer cell (Nishimura, S. et al., *Biochem. J.* 243:313–327 (1987); Bos, J. L., *Cancer Res.* 49:4682–4689 (1989)).

The desire to increase the utility and applicability of such assays is often frustrated by assay sensitivity as well as complexity and cost. Hence, it would be highly desirable to develop more sensitive as well as simple and relatively inexpensive assays for detection of alterations in DNA.

Nucleic acid detection assays can be based on any of a number of characteristics of a nucleic acid molecule, such as its size, sequence, susceptibility to digestion by restriction endonucleases, etc. The sensitivity of such assays may be increased by altering the manner in which detection is reported or signaled to the observer. Th Most methods devised to attempt to detect genetic alter-
ations consisting of one or a few bases involve hybridization
between a standard nucleic acid (DNA or RNA) and a test
DNA such that the mutation is revealed as a mispaired or
unpaired base in a heteroduplex molecule. Detection of
these mispaired or unpaired bases has been accomplished by
a variety of methods. Mismatches have been detected by
means of enzymes (RNaseA, MutY) which cut one or both
strands of the duplex at the site of a mismatch (Myers, R. M.
et al., *Cold Spring Harbor Symp. Quant. Biol.* 51:275–284
(1986); Gibbs, R. et al., *Science* 236:303–305 (1987); Lu, A.
S. et al., 1992, *Genomics* 14:249–255 (1992)). Duplexes
without mismatches are not cut. By using radioactively labeled nucleic acid fragments to anneal to a test DNA, it is possible to use these enzymes to generate specific size fragments when a mutation is present in the test DNA. The fragments are distinguished from uncut fragments by means of polyacrylamide gel electrophoresis. The major problems with these methods are that they require the use of RNA (RNase method) or have the ability to detect only a limited number of mismatches (MutY method).

Mismatch-containing DNA duplexes have also been dis-
tinguished from perfectly matched duplexes by means of
denaturing gel electrophoresis. In this system, duplexes are
run on a polyacrylamide gel in a denaturing gradient under
conditions where mismatch-containing DNA denatures
more readily than the identical duplex lacking a mismatch,
such that the two kinds of duplexes migrate differently. This
method, while sensitive and accurate, is extremely laborious
and requires a high level of technical sophistication.

Two other methods of mutation detection depend on the
failure to extend or join fragments of DNA when mis-
matches are present. Both require the use of standard DNA
oligonucleotides that end precisely at the site of the mutation
in question such that, when annealed to test DNA, it is the
last base of the oligonucleotide which is mismatched. Mis-
match detection depends either on (a) the inability of DNA
polymerase to extend an oligonucleotide with a mismatched
terminal base or (b) the inability of DNA ligase to join two
oligonucleotides when there is a mismatch at the joint
between them. Fragment length is determined by gel elec-
trophoresis. Presence of longer fragments than the input
oligonucleotides indicates that a mismatch, i.e., mutation,
was not present in the test DNA. These methods are also
somewhat laborious, require that the exact location of the
mutation be known and are difficult to interpret when the
sample DNA is heterozygous for the mutation in question.
Therefore, they are not practical for use in screening for
polymorphisms.

A chemical method for cleavage of mismatched DNA
(Cotton, R. G. et al., *Proc. Natl. Acad. Sci. USA*
85:4397–4401 (1988); Cotton, R. G., *Nuc. Acids Res*
17:4223–4233 (1989)) is based on chemical cleavage at a
mismatch site in a DNA-DNA heteroduplex, using a number
of agents, in particular osmium tetroxide and hydroxy-
lamine. In this method DNA probes are prepared by restric-
tion enzyme cleavage of DNA of interest. Plasmid DNA
containing the sequence of interest is hybridized to labeled
probe DNA (either end-labeled or internally labeled with
$^{32}$P). Hydroxylamine chemically modifies mismatched
cytosines; osmium tetroxide modifies mismatched thymines.
Piperidine is then used to cleave the DNA at the modified
sites, followed by polyacrylamide gel electrophoresis
(PAGE) and autoradiography to identify the cleavage prod-
ucts. This method is said to have the advantage of detecting
all possible single base pair mismatches because, the method
also results in cleavage at a matched base pair in the vicinity
of a mismatch.

Publications from Caskey's laboratory (Caskey, C. T. et
al., European Patent Publication 333,465 (Sep. 20, 1989);
Grompe, M. et al., *Proc. Natl. Acad. Sci. USA* 86:5888–5892
(1989)) disclose a method for localizing a mutation which
utilizes PCR-amplified cDNA as a source of template for the
mismatch cleavage reaction. This technique was success-
fully applied in studying ornithine transcarbamoylase
(OTCase) deficiency patients to map mutations.

Kung et al., U.S. Pat. No. 4,963,658, discloses detection
of single stranded DNA (ssDNA) by binding with a high-
affinity ssDNA-binding protein, such as a topoisomerase or a DNA unwinding protein which itself can be bound to a label, such as β-D-galactosidase.

Mismatch Repair Systems and Mismatch Binding Proteins

DNA mismatch repair systems employ a family of proteins including proteins which recognize and bind to mismatch-containing DNA, which are designated mismatch binding proteins (MBPs). For reviews, see Radman, M. et al., *Annu. Rev. Genet.* 20:523–538 (1986); Radman, M. et al., *Sci. Amer.*, August 1988, pp. 40–46; Modrich, P., *J. Biol. Chem.* 264:6597–6600 (1989)). The MutS protein was identified as such a component of the *E. coli* mismatch repair system. See, for example, Lahue, R. S. et al., *Science* 245:160–164 (1989); Jiricny, J. et al., *Nucl. Acids Res.* 16:7843–7853 (1988); Su, S. S. et al., *J. Biol. Chem.* 263:6829–6835 (1988); Lahue, R. S. et al., *Mutat. Res.* 198:37–43 (1988); Dohet, C. et al., *Mol. Gen. Genet.* 206:181–184 (1987); and Jones, M. et al., *Genetics* 115:605–610 (1987). Analogous proteins are known in other bacterial species including MutS in *Salmonella typhimurium* (Lu, A. L. et al., *Genetics* 118:593–600 (1988); Haber L. T. et al., *J. Bacteriol.* 170:197–202 (1988); Pang, P. P. et al., *J. Bacteriol.* 163:1007–1015 (1985)) and the hexA protein of *Streptococcus pneumoniae* (Priebe S. D. et al., *J. Bacteriol.* 170:190–196 (1988); Haber et al., supra).

Purified MutS protein binds DNA containing mispaired bases, but does not bind DNA without mismatches or single-stranded DNA. The MutS-DNA interaction does not result in any degradation or modification of the DNA. None of the above references disclose the possibility of using a MBP or immobilized MBP as part of a mutation detection assay or for purposes of removing mismatched DNA from amplified DNA samples.

SUMMARY OF THE INVENTION

The present inventor has conceived of the use of immobilized mismatch binding protein (MBP), for example, the MutS protein of *E. coli,* for (1) the detection of genetic mutations or genomic polymorphisms, (2) the purification of amplified DNA samples by removing contaminating sequences and sequences containing errors introduced during the amplification processes, and (3) the identification of specific alleles in multi-allelic systems.

The nucleic acid, preferably DNA, being analyzed can be obtained from any source, including blood cells, tumor tissues, cells in culture or any tissue, and can be obtained from any species including humans.

The DNA may be labeled by any of a variety of well-known methods, using calorimetric, chemiluminescent or radioactive markers. In fact, it is not necessary to label test DNA at all.

For detection of mutations or polymorphism, the assay can be performed with a labeled competing oligonucleotide. For purification of amplified DNA, no label is required. For allele identification, the label must be in a synthesized single-stranded oligonucleotide probe.

The methods of the present invention depend on the creation of mismatches in the test DNA which are revealed by denaturing the test DNA and allowing it to reanneal. When testing for heterozygosity or for polymorphism within a test DNA sample, the test DNA can simply be self-annealed, resulting in formation of mismatches when the single strands reanneal with a strand descended from the other parental chromosome. If no heterozygosity exists, no mismatches will be formed. In this case, the label can be in the primers used for amplification or may be added to the termini of the test DNA if amplification is not required.

A similar procedure and labeling scheme is used to remove sequences containing errors introduced during amplification of DNA or minority sequence species. In these cases, the material which does not bind to the MBP is recovered, and contains only those duplex sequences without mismatches. These sequences will therefore be greatly enriched for the majority sequence in the amplified population. When the starting material contains only one sequence, the unbound material will contain those sequences which are identical to the starting material, while those sequences containing errors introduced during amplification will, provided they are relatively rare, have formed mismatches which are retained by the immobilized MBP.

To detect homozygous mutations, it is necessary to anneal the test DNA in the presence of known wild-type sequences. Such sequences can be synthesized artificially or created during amplification by adding known wild-type sequences to the starting material before amplification. When annealing is performed in the presence of known wild-type sequences, the assay will detect both homozygous and heterozygous mutations.

For allele identification, it is necessary to add a labeled single-stranded probe DNA to the test DNA after amplification. The probe sequence must be identical to the allele of interest such that no mismatches are formed when it anneals to DNA of that allele. The sequence of the probe is selected so that it forms mismatches when annealed to the DNA of any other allele. When test DNA is annealed to such a probe (with the test DNA in excess such that the probe sequences all anneal to form a duplex) and exposed to excess immobilized MBP, the presence of unbound label indicates that the allele in question is present in the test DNA sample.

Thus, the present invention is directed to a method for detecting a mutation from a non-mutated sequence of a target polynucleotide, preferably DNA, in a sample, comprising:

(a) incubating a detectably labeled polynucleotide or oligonucleotide from the sample with an immobilized mismatch-binding protein under conditions in which mismatch-containing polynucleotide molecules bind to the immobilized protein; and (b) detecting the binding of any mismatch-containing polynucleotide from the sample to the mismatch-binding protein, whereby the presence of detectably labeled polynucleotide or oligonucleotide bound to the mismatch-binding protein is indicative of a mutation in the sequence of the target polynucleotide.

Also provided is a method for detecting a mutation from a non-mutated sequence of a double stranded target mammalian polynucleotide in a sample, comprising:

(a) denaturing any double stranded polynucleotide in the sample followed by allowing DNA strands to reanneal;

(b) incubating the denatured and reannealed double stranded nucleotide of step (a) with a mismatch-binding protein immobilized on a solid support, either (i) in the presence of a detectably labeled mismatch-containing oligonucleotide capable of binding to the MBP; or (ii) wherein the MBP was preincubated with and allowed to bind a detectably labeled mismatch-containing oligonucleotide; and (c) detecting the amount of detectably labeled mismatch-containing oligonucleotide bound to the mismatch-binding protein whereby the presence of a mutation in the double stranded mammalian polynucleotide of the sample results in a decrease in the binding of the detectably labeled oligonucleotide to the mismatch-binding protein.

A preferred MBP in the above methods is the E. coli MutS protein or a functional derivative thereof.

Preferred solid supports include, but are not limited to, modified cellulose, polystyrene, polypropylene, polyethylene, dextran, nylon, polyacrylamide and agarose. A most preferred solid support is a nitrocellulose membrane.

A preferred detectable label in the above methods is biotin.

Also provided is a method for the removal from an amplified DNA sample of minority sequences and sequences containing sequence errors introduced during the process of amplification, which method comprises:

(a) subjecting the amplified DNA sample to conditions of denaturation followed by reannealing, such that minority sequence or error-containing sequences form mismatch-containing DNA duplexes, thereby generating a mixture containing mismatched duplexes;

(b) incubating the mixture of step (a) with an immobilized mismatch-binding protein so that mismatch-containing duplexes bind to the MBP; and (c) removing the immobilized MBP to which mismatch-containing DNA has bound from the amplified DNA sample, thereby removing the sequences containing sequence errors.

In another embodiment is provided a method for identifying a specific allele in a multi-allelic system in a sample of amplified DNA, comprising:

(a) mixing a detectably labeled oligonucleotide probe which is perfectly complementary to the DNA sequence of the specific allele with an excess of amplified test DNA under conditions of denaturation followed by annealing such that, after denaturing and annealing, every copy of the probe will be found in a duplex DNA;

(b) incubating the mixture of step (a) with an excess of immobilized MBP such that all mismatch-containing DNA is retained on the immobilized MBP;

(c) removing said immobilized MBP to which has bound any mismatch-containing DNA from the amplified test DNA; and (d) detecting the presence of the detectable label in the sample from which the immobilized MBP has been removed, wherein, the presence of labeled DNA in the sample indicates that the probe is perfectly complementary to an allele in the test DNA.

In the above methods, the immobilized MBP may be (a) in a form which is removable by centrifugation, or (b) immobilized onto a column support material wherein the flow through material is devoid of mismatch-containing duplexes, or (c) immobilized on a filter support such the filtrate is devoid of mismatch-containing duplexes.

The present invention is also directed to a kit useful for detecting a mutation from a non-mutated sequence of a target polynucleotide sequence in a sample, the kit being adapted to receive therein one or more containers, the kit comprising:

(a) a first container containing an immobilizable mismatch-binding protein;

(b) a second container containing a solid support capable of immobilizing the MBP; and (c) a third container or a plurality of containers containing a reagent or reagents capable of detecting the binding of a detectably labeled mismatch-containing nucleic acid hybrid to the mismatch-binding protein.

Also provided is a kit useful for detecting a mutation from a non-mutated sequence of a target polynucleotide sequence in a sample, the kit being adapted to receive therein one or more containers, the kit comprising:

(a) a first container containing a mismatch-binding protein immobilized on a solid support; and (b) a second container or a plurality of containers containing a reagent or reagents capable of detecting the binding of a detectably labeled mismatch-containing nucleic acid hybrid to the mismatch-binding protein.

In the above kits, the MBP is preferably MutS or a functional derivative thereof. The solid support is preferably selected from the group consisting of natural cellulose, modified cellulose, most preferably nitrocellulose, or polystyrene, polypropylene, polyethylene, dextran, nylon, polyacrylamide and agarose.

DESCRIPTION OF THE PREFERRED EMBODIMENTS

Figure 1:
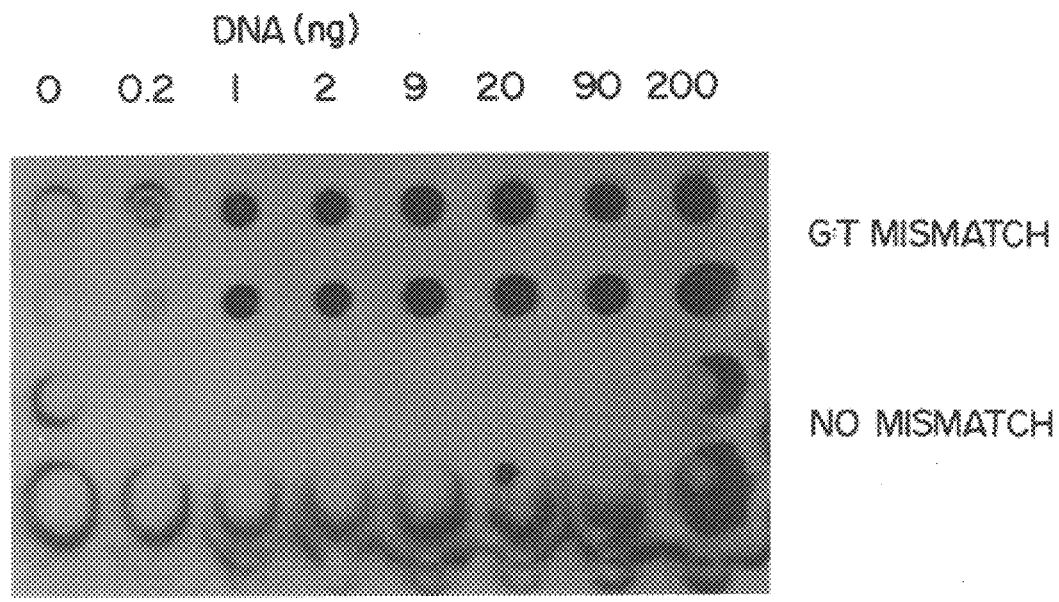
FIG. 1 shows the results of a direct assay of mismatches using nitrocellulose-bound MutS. Increasing amounts of biotinylated mismatch-containing DNA (upper 2 lines) or mismatch-free DNA (lower 2 lines) were added to the reaction mixtures.

The present inventor conceived of a new, broadly applicable and relatively simple method for detecting a single base change in a DNA sequence or several such base changes. This method is based upon the formation of a mismatch-containing heteroduplex when a strand of mutant DNA and a "complementary" strand of wild-type DNA hybridize.

The presence of the mismatch is detected in a highly specific manner by first allowing the DNA to bind to an immobilized mismatch-binding protein (MBP), such as the MutS protein of E. coli. The presence of DNA bound to the MBP is then detected in any of a number of ways, depending on the label used and whether the assay is a direct assay or a competitive assay. This method stands in stark contrast to methods of the prior art which employ mismatch cutting nuclease enzymes capable of breaking DNA at or near a mispaired base pair.

The methods described herein provide a mutation/polymorphism detection system having the advantages of (a) simplicity, (b) accuracy, (c) ability to be used without radioactivity, (d) ability to detect all single base substitution mutations and addition or deletion mutations of 1–4 bases.

Standard reference works setting forth the general principles of recombinant DNA technology and cell biology, and describing conditions for isolation and handling of nucleic acids, denaturing and annealing nucleic acids, hybridization assays, and the like, include: Sambrook, J. et al., *MOLECULAR CLONING: A LABORATORY MANUAL,* 2nd Edition, Cold Spring Harbor Press, Cold Spring Harbor, N.Y., 1989; Albers, B. et al., *MOLECULAR BIOLOGY OF THE CELL,*

2nd Ed., Garland Publishing, Inc., New York, N.Y., 1989; Watson, J. D., et al., *MOLECULAR BIOLOGY OF THE GENE,* Volumes I and II, Benjamin/Cummings Publishing Co., Inc., Menlo Park, Calif., 1987; Darnell, J. E. et al., *MOLECULAR CELL BIOLOGY,* Scientific American Books, Inc., New York, N.Y., 1986; Lewin, B. M., *GENES II,* John Wiley & Sons, New York, N.Y., 1985, which references are hereby incorporated by reference in their entirety.

MBPs are proteins of around 100 kDa, have been identified in and isolated from both bacteria and higher organisms and selectively bind DNA containing mismatched bases. MBPs have been found in yeast (Valle G et al., 1991 *Yeast* 7:981–988; Miret J. J. et al., 1993, *J. Biol Chem.* 268:3507–3513), as well as in humans (Stephenson, C. et al., 1989, *J. Biol. Chem.* 264:21177–21782; Karran, P et al., 1990, *Mutat. Res.* 236:269–275; Hughes M. J. et al., 1992, *J. Biol. Chem.* 267:23876–23882; Reenan, A. G. et al., 1993, *Genetics* 132:963–973; Reenan, A. G. et al., 1993, *Genetics* 132:975–985). Mismatch binding proteins from Xenopus and from mouse have been cloned by M. Radman and colleagues.

A preferred MBP is characterized by its ability to bind DNA-DNA (or DNA-RNA or RNA-RNA) duplexes containing mispaired or unpaired bases, to the significant exclusion of single stranded polynucleotides or perfectly matched duplexes. In a preferred embodiment, the intact native MutS protein from *E. coli* is used. However, as used herein, the term "mismatch binding protein" or "MBP" is intended to encompass a functional derivative of the intact, native protein. By "functional derivative" is meant a "fragment," "variant," "analog," or "chemical derivative" of the protein which retains the ability to bind to a mismatch-containing nucleic acid heteroduplex, which permits its utility in accordance with the present invention.

A "fragment" of a MBP refers to any subset of the molecule, that is, a shorter peptide. A "variant" of the protein refers to a molecule substantially similar to either the entire protein or a DNA-hybrid-binding fragment thereof. A variant of a mismatch-binding protein, for example, of MutS, may be prepared by recombinant DNA methods well-known in the art.

A preferred functional derivative of MutS is a homologue of *E. coli* MutS in another species, such as the MutS protein of *Salmonella typhimurium* (Lu, A. L. et al., supra; Haber L. T. et al., supra; Pang, P. P. et al., supra) or the hexA protein of *Streptococcus pneumoniae* (Priebe S. D. et al., supra; Haber et al., supra). In addition, possible eukaryotic homologues of MutS or HexA can also be used, such as those encoded by the homologous sequences identified in human, mouse, frog or hamster DNA (Shimada, T. et al., *J. Biol. Chem.* 264:20171 (1989); Linton, J. et al., *Molec. Cell. Biol.* 7:3058–3072 (1989); Fujii, H. et al., *J. Biol. Chem.* 264:10057 (1989)).

A "chemical derivative" of the MBP contains additional chemical moieties not normally a part of the protein, including additional stretches of amino acids as in a fusion protein. Covalent modifications of the peptide are included within the scope of this invention. Such modifications may be introduced into the molecule by reacting targeted amino acid residues of the protein with an organic derivatizing agent that is capable of reacting with selected side chains or terminal residues.

In selecting a protein as being a useful MBP for the methods of the present invention, assays can be performed by one of ordinary skill in the art using conventional methods. Thus, for example, in evaluating a sample for the presence of a MBP useful in the present invention, one can perform a mismatch binding assay, such as that described for MutS by Jiricny et al. (which reference is hereby incorporated by reference in its entirety). Preferably, a filter binding assay is used. To prepare the oligonucleotide heteroduplex, an oligonucleotide, preferably of about 16 bases is labeled with $^{32}P$ using a kinase reaction and $\gamma$-$^{32}P$-ATP using a kinase such as T4-polynucleotide kinase. The 5'-labeled oligonucleotide (which can be stored at −20° C.) is then annealed with a complementary oligonucleotide having a single base pair mismatch under standard conditions. The annealed 16 base pair heteroduplex is mixed with an excess of the protein being tested and kept on ice for 30 minutes. The mixture is then applied to a nitrocellulose filter which has been prewetted in the assay buffer. Gentle suction is applied for several seconds, and the filter is washed extensively with ice-cold assay buffer. The filter is then dried in air, suspended in scintillation fluid and counted. By virtue of the protein sticking to the filter, any counts on the filter can be attributed to binding to the putative MBP. In the absence of such a protein, the labeled oligonucleotide heteroduplex will pass through the filter. Thus, by using such a simple assay, one can easily detect and select a MBP useful in the methods of the present invention.

As used in the present invention, the MBP is immobilized to a solid support or carrier. By "solid support" or "carrier" is intended any support capable of binding a protein. Well-known supports or carriers include natural cellulose, modified cellulose such as nitrocellulose, polystyrene, polypropylene, polyethylene, dextran, nylon, polyacrylamide, and agarose or Sepharose®. Also useful are magnetic beads. The support material may have virtually any possible structural configuration so long as the immobilized MBP is capable of binding to the target nucleic acid molecule. Thus, the support configuration can include microparticles, beads, porous and impermeable strips and membranes, the interior surface of a reaction vessel such as test tubes and microtiter plates, and the like. Preferred supports include nitrocellulose disks or strips. Those skilled in the art will know many other suitable carriers for binding the MBP or will be able to ascertain these by routine experimentation.

Most preferred is a solid support to which the MBP is attached or fixed by covalent or noncovalent bonds. Preferably, noncovalent attachment is by adsorption using methods that provide for a suitably stable and strong attachment. The MBP is immobilized using methods well-known in the art appropriate to the particular solid support, providing that the ability of the MBP to bind mismatch-containing DNA is not destroyed.

The immobilized MBP is then easily used to detect heterozygosity (or polymorphism) as well as single base mutations, or to isolate mismatch-containing DNA from a mixture, or to rid a mixture of mismatch-containing DNA.

In one embodiment, the surface of polystyrene or other plastic multiwell plates serves as the solid support. In another embodiment, a solid support to which the MBP is bound is affixed to the bottom of wells of multiwell plates.

In a preferred embodiment, the immobilization and DNA binding can be performed in a 96 well blotting apparatus and the resulting sheet of nitrocellulose (or other support) paper can be removed to evaluate reactions. For example, color development on the nitrocellulose can be used to evaluate binding based on an enzyme as part of the detection system and a chromogenic or chemiluminescent substrate for the enzyme serving as the precursor of the color reactions.

Following attachment of the MBP to the support, the support is treated ("blocked") to prevent further binding of proteins or nucleic acids, using methods and reagents well-known in the art.

The immobilized MBP is contacted with and allowed to bind (to saturation) small oligonucleotide heteroduplex molecules. The oligonucleotides preferably have about 30 base pairs. For testing, a DNA duplex containing a mismatch which is well recognized (i.e., bound) by the MBP is used.

Preparation of Oligonucleotides Containing or Lacking Mismatches

Such oligonucleotides are prepared using a nucleotide modified at the 5' end with a detectable label such that they can be quantitatively detected by appropriate detection methods, preferably spectrophotometry or chemiluminescence. In a preferred embodiment, the oligonucleotide is biotin-modified, and is detectable using a detection system based on avidin or streptavidin which binds with high affinity to biotin. The streptavidin can be conjugated to an enzyme, the presence of which is detected using a chromogenic substrate and measuring the color developed.

Examples of useful enzymes in the methods of the present invention are horseradish peroxidase, alkaline phosphatase, glucose-6-phosphate dehydrogenase, malate dehydrogenase, staphylococcal nuclease, delta-V-steroid isomerase, yeast alcohol dehydrogenase, α-glycerophosphate dehydrogenase, triose phosphate isomerase, asparaginase, glucose oxidase, β-galacto-sidase, ribonuclease, urease, catalase, glucoamylase and acetylcholinesterase.

The detectable label may also be a radioisotope which can be detected by such means as the use of a gamma counter or a scintillation counter or by autoradiography.

The detectable label may also be a fluorescent compound. When the fluorescently labeled molecule is exposed to light of the proper wave length, its presence can then be detected due to fluorescence using microscopy or fluorometry. Among the most commonly used fluorescent labelling compounds are fluorescein isothiocyanate, rhodamine, phycoerythrin, phycocyanin, allophycocyanin, o-phthaldehyde and fluorescamine.

The detectable label may be a fluorescence emitting metal such as $^{152}$Eu, or others of the lanthanide series. These metals can be attached to the oligonucleotide using metal chelating groups such as diethylenetriaminepentaacetic acid or ethylenediaminetetraacetic acid.

The detectable label may be a chemiluminescent compound. The presence of the chemiluminescent-tagged molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the oligonucleotide. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

A MBP bound to the DNA-DNA, DNA-RNA or RNA-RNA hybrid can be detected either directly or indirectly. For direct detection, the poly- or oligonucleotide duplex is detectably labeled using labels as discussed herein.

For indirect detection, the assay utilizes competition of binding to the MBP of the test DNA with an already bound or a contemporaneously exposed mismatch-containing duplex. Thus, a labeled mismatch-containing oligonucleotide is pre-bound to the MBP or is incubated together with the MBP and test DNA. The more mismatch-containing DNA in the test sample, the less binding of the labeled oligonucleotide to the MBP will occur.

The test sample to be assayed can be in any medium of interest, and will generally be a sample of medical, veterinary, environmental, nutritional, or industrial significance. Human and animal specimens and body fluids particularly can be assayed by the present method, providing that they contain cells from which nucleic acids can be prepared. Preferred sources include blood, sperm, other tissue, milk, urine, cerebrospinal fluid, sputum, fecal matter, lung aspirates, throat swabs, genital swabs and exudates, rectal swabs, and nasopharyngeal aspirates.

Detection of Heterozygosity or Polymorphism

To detect heterozygosity or polymorphism in DNA from a diploid organism, test DNA is preferably prepared by denaturing and annealing PCR-amplified DNA from a diploid organism. The test DNA is prepared with labeled primers, annealed and added to a well or other reaction vessel which contains immobilized MBP already bound to mismatched oligonucleotides. Alternatively, test DNA can be mixed with mismatched oligonucleotides and the mixture added to a well or other vessel containing immobilized MBP A spectrophotometric reading is made at the wavelength appropriate for quantitative detection of the test DNA. After an incubation period suitable to allow either (1) binding of the test DNA to the immobilized MBP or (2) displacement of the mismatched oligonucleotide from the immobilized MBP, the DNA solution is removed, the well washed, and a spectrophotometric reading made at the wavelength appropriate for quantitative detection of the bound mismatched oligonucleotide.

The ratio of the reading for test DNA to the reading for the mismatched oligonucleotide will be vastly different for mismatch-containing and mismatch-free test DNA over a wide range of DNA concentrations.

Standard curves are prepared using known quantities of DNA to allow characterization of test DNA as homozygous or heterozygous without having to quantitate the test DNA prior to the assay. Thus, a single DNA sample is sufficient to determine heterozygosity and a single 96 well microplate will allow the testing of at least about 80 different DNA samples.

Detection of Homozygous Mutations

To detect homozygous mutations, known homozygous wild-type DNA must be combined with the test DNA sample before denaturing and annealing. Only test DNA containing a mutation (homozygous) will form mismatch-containing DNA that can compete with the mismatched oligonucleotide for binding to the immobilized MBP.

The method of the present invention can be used with (a) only the mismatched oligonucleotide labeled or (b) only the test DNA labeled. However, both of these methods require that the nucleic acid concentration be determined and that the test be performed at several different test DNA concentrations.

When the mismatched oligonucleotides are labeled, the test is based on competition with several different concentrations of test DNA and comparison of the resulting curve (with concentration expressed as moles of duplex molecules) with standard curves for mismatched and non-mismatched standards.

When the test DNA is labeled, the test involves measuring the extent of binding to the MBP of several concentrations below saturation and comparison of the resulting curve with standard curves for mismatched and non-mismatched standards.

Purification of Amplified DNA Samples

One of the most revolutionary and widely used technologies currently employed in modern molecular biology is the process of polymerase chain reaction (PCR), which amplifies DNA sequences from starting amounts so minute as to be nearly undetectable. For reviews of PCR, see: Mullis, K. B., 1986, *Cold Spring Harbor Symp. Quant. Biol.* 51:263–273; Saiki, R. K. et al., 1985, *Bio/Technology* 3:1008–1012; and Mullis, K. B. et al., 1987, *Meth. Enzymol.* 155:335–350. In addition, because PCR can amplify specific sequences, it allows the purification of specific sequences, basically in a single step, from genomic DNA. PCR is an essential component of virtually all studies of the human genome, is a central component of gene identification and cloning, is increasingly used in the diagnosis of genetic and infectious diseases and is widely used in forensics.

However, for some applications, in particular, gene cloning and mutation detection, PCR suffers from an inherent tendency of the polymerases to make mistakes by inserting incorrect, non-complementary bases during synthesis. Although the fidelity of most replicative polymerases in vivo is such that they insert only one incorrect base for every $10^{10}$ bases replicated, polymerases used in PCR can have error rates as high as one incorrect base for every $10^4$ bases replicated. This high an error rate can mean that a significant fraction of the amplified molecules will not be identical in sequence with the starting material.

The present methods are useful for purifying amplified DNA samples using an immobilized MBP to remove minority sequences and molecules containing sequence alterations introduced by the amplification process. For example, if a DNA segment is amplified through 20 rounds of replication (a common amount of amplification), a significant fraction of the final molecules may contain one or more incorrect bases. In cloning experiments, this greatly increases the risk of cloning a nucleotide sequence different from the starting sequence.

In mutation detection assays involving denaturation and annealing of a PCR-amplified sample, incorrect bases inserted during PCR may be scored as if they were mutations in the original sample. Thus, for accurate mutation detection it is necessary to eliminate all DNA molecules with sequence alterations introduced by PCR copy errors. The method described here accomplishes this purification in a simple and straight-forward manner.

Immobilized MBP can be used to purify amplified DNA samples. MBP is immobilized by binding to solid phase supports, preferably nitrocellulose filters, sepharose beads or magnetic beads. The filters or beads are treated, if necessary, to prevent the binding of double-stranded DNA. The amplified DNA sample is denatured, by heating, and allowed to reanneal. Given the random nature of PCR mistakes, virtually all incorrect bases will be found in mismatched base pairs after annealing.

The immobilized MBP is added to the sample and the solution mixed by gentle shaking. The immobilized MBP, and any bound mismatch-containing DNA, is removed, for example, by removing the filter, by allowing the beads to settle out of solution or by removing the beads magnetically, depending on the nature of the solid support used. This leaves behind precisely matched DNA duplexes.

In addition to purifying amplified DNA samples by removing molecules containing errors introduced during amplification, purification using an immobilized MBP is used to enrich for majority sequences when samples of diverged, repeated DNA sequences, such as of immunoglobulin genes, are being examined.

To remove completely a minority species from a sample amplified from a mixed population of DNA (with respect to sequence), it may be necessary to perform more than one round of purification as described herein and possibly more than one round of amplification.

Note that the present method can be used to purify sequences from both homozygous and heterozygous amplified sequences, since half of the parental sequences in a heterozygous sample will anneal to the complementary strand of the same parental heritage and thus form a molecule without mismatches. In other words, when the starting material is heterozygous, half of the annealed molecules will be removed from the sample because they contain a mismatch due to differences in the starting sequences. However, half the annealed molecules will not contain such mismatches and so will be removed from the sample only if they contain mismatches which were created as a result of errors during amplification. In any event, mutation detection assays will require a second round of denaturing and annealing.

Allele Identification in Multi-allelic Systems

As more alleles of disease-causing genes are identified, and in the quest to develop a polymorphism map of the human genome, it is becoming increasingly important to be able to identify particular alleles of a given gene. Immobilized MBPs provide a simple and straightforward means of allele identification.

Unique, labeled oligonucleotide probes are prepared for each allele of a given gene, such that the probe is perfectly complementary to only one allele, i.e., the probe will form one or more mismatches when paired with an incorrect allele. The probe is mixed with an excess of amplified test DNA such that, after denaturing and annealing, every copy of the probe will be found in duplex. The process is repeated with probes for every allele in question. The annealed DNA mixture is then either:

(1) mixed with immobilized MBP on a support that can be removed from the suspension by centrifugation;

(2) passed through a micro-column of immobilized MBP on an appropriate column support; or (3) passed through a filter support containing immobilized MBP.

In any case, the immobilized MBP must be in excess such that all mismatch-containing DNA is retained. The supernatant, column flow through or filtrate is analyzed for the presence of label. Only in those cases where the probe is perfectly complementary to an allele in the test DNA will label be detected.

In order to be certain that no single-stranded probe sequences are present, it may be necessary, or at least desirable, to include some single-stranded DNA binding component on the support for the immobilized MBP. This system works equally well for homozygous or heterozygous conditions.

Kits

The present invention is also directed to a kit or reagent system useful for practicing the methods described herein. Such a kit will contain a reagent combination comprising the essential elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and usually including written instructions for the performance of assays. The kit of the present invention may include any configurations and compositions for performing the various assay formats described herein.

In all cases, the reagent system will comprise (1) an immobilizable or immobilized MBP or functional derivative, preferably mutS, and (2) additional reagents useful in carrying out the assay. The kit may optionally contain labeled mismatch-containing oligonucleotides. For detecting a particular mutation, a kit may also contain labelled primers for carrying out a PCR. A kit according to the present invention can additionally include ancillary chemicals such as the components of the solution in which binding of duplexes to the immobilized MBP takes place.

Having now generally described the invention, the same will be more readily understood through reference to the following examples which are provided by way of illustration, and are not intended to be limiting of the present invention, unless specified.

EXAMPLE I

BINDING OF MISMATCH-CONTAINING DNA BY IMMOBILIZED MISMATCH BINDING PROTEIN

A. Materials and Methods

1. Preparation of Immobilized MEP

A nitrocellulose sheet (0.45 μm, Schleicher & Schull) was wet with reaction buffer (20 mM Tris pH 7.6, 0.01 mM EDTA, 5 mM MgCl$_2$, 0.1 mM DTT) and placed in a dot blot apparatus (Bio-Rad).

Purified MBP, E. coli MutS, at a concentration of 0.5 μg/10 μl reaction buffer was spotted on the nitrocellulose paper in each well. The wells were incubated at room temperature, and the remaining liquid was pulled through with vacuum. Each well was washed twice with 100 μl reaction buffer by adding the solution to the well and then pouring it out. After the second wash, the remaining solution was pulled through the vacuum.

2. Blocking

The nitrocellulose filter was blocked with bovine serum albumin (BSA) to prevent the binding of other proteins or nucleic acids. Reaction buffer (200 μl) containing 1% (w/v) BSA was added to each well. After 1 hour at room temperature, the solution was poured out and each well washed with 2×100 μl reaction buffer by adding the solution to the well and then pouring it out. After the second wash, the remaining liquid was pulled through with vacuum.

3. Oligonucleotides

The sequence of the oligonucleotides used in these studies was taken from the 30 base region surrounding the site of the sickle cell mutation in the human β-globin gene. The mismatch is at the site of the sickle cell mutation, although the mutant sequence used to form the mismatch is not the sickle cell mutation (the actual sickle cell mutation is an A:T→T:A transversion). Biotinylated oligonucleotides were biotinylated on the 5' end of the mutant strand. Biotinylation is accomplished during synthesis by adding a biotin-modified nucleotide to the 5' end of the oligonucleotides.

```
G:T Mismatch:
Mutant      GCACCTGACT CCTGGGGAGA AGTCTGCCGT [SEQ ID NO:1]
Wild-type   CGTGGACTGA GGACTCCTCT TCAGACGGCA [SEQ ID NO:2]

No Mismatch:
Mutant      GCACCTGACT CCTGGGGAGA AGTCTGCCGT [SEQ ID NO:1]
Mutant      CGTGGACTGA GGACCCCTCT TCAGACGGCA [SEQ ID NO:3]
```

4. Binding DNA

Biotinylated oligonucleotides, in 20 μl reaction buffer containing 1% BSA, were added to each well. After 30 minutes at room temperature, remaining liquid was poured out. Each well was washed with 5×100 μl reaction buffer by adding the solution to the well and then pouring it out. After the fifth wash, the remaining solution was pulled through by vacuum.

5. Binding Streptavidin-conjugated Horse Radish Peroxidase (HRP)

The presence of biotin was detected by its binding of Streptavidin. A 100 μl volume of Streptavidin-conjugated HRP (Pierce Chemicals) at a concentration of 50 mg/ml in reaction buffer +1% BSA was added to each well. After 2 hours at room temperature, the solution was poured out and each well washed with 5×100 μl reaction buffer by adding the solution and then pouring it out. After the fifth wash, the remaining solution was pulled through with vacuum.

6. Enhanced ChemiLuminescence® (ECL) Development

The nitrocellulose sheet was removed from dot blot apparatus and washed 3 times in a petri dish with 10 ml reaction buffer. Five ml ECL development solution (Amersham) was poured over the nitrocellulose. The substrate for HRP in this reagent is a chemiluminescent compound. After 1 minute, the solution was removed. The nitrocellulose was blotted dry and placed between 2 clear plastic sheets. The nitrocellulose thus protected was exposed to X-ray film in the dark for varying periods of time. In the experiments reported here, the exposure time was 1 minute.

7. Competition

In competition studies, the DNA binding was as described above, except that a constant amount of biotinylated mismatch-containing oligonucleotide (5 ng) was mixed with varying amounts of unlabeled DNA, with or without a mismatch, and added to the wells.

B. Results

1. Specific Binding of Mismatch-containing DNA by Immobilized MBP

FIG. 1 shows the results (in duplicate) of adding increasing amounts of biotinylated mismatch-containing DNA (upper 2 lines) or mismatch-free DNA (lower 2 lines).

The immobilized MBP can detect as little as 0.2 ng of mismatch-containing 30-mer, whereas no detectable binding of mismatch-free 30-mer was observed even with 200 ng of DNA. (The lines around the lower spots were artifacts of incomplete washing.)

2. Competition Assay

Figure 2:
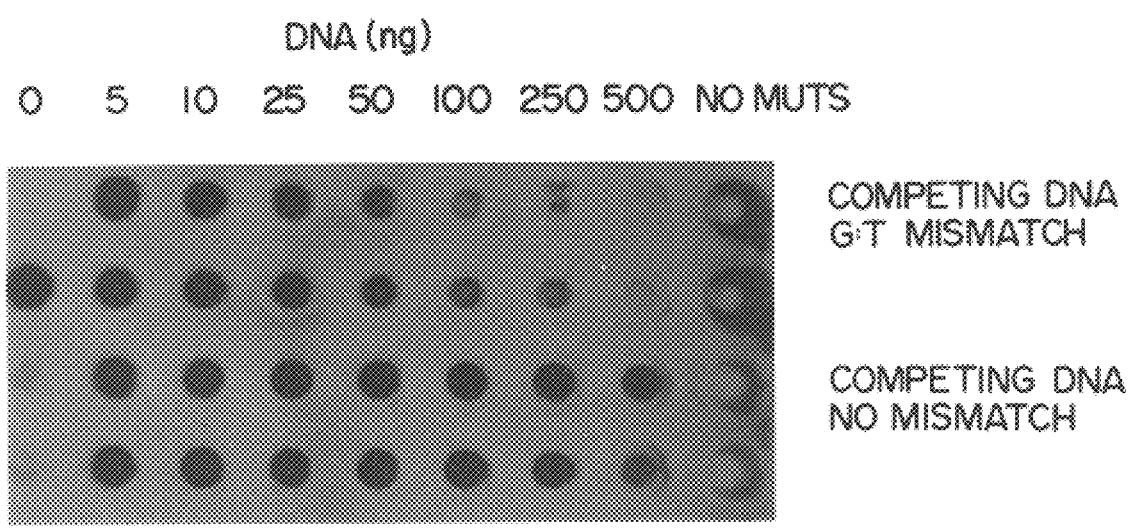
FIG. 2 shows the results of a competition assay of mismatched duplexes using nitrocellulose-bound MutS protein. Increasing amounts of unlabeled mismatch-containing 30-mer (upper 2 lines) or mismatch-free 30-mer (lower 2 lines) were added to 5 ng biotinylated mismatch-containing 30-mer. The far right column on the figure represents wells which contained no MutS.

FIG. 2 shows the results (in duplicate) of adding increasing amounts of unlabeled mismatch-containing 30-mer (upper 2 lines) or mismatch-free 30-mer (lower 2 lines) to 5 ng biotinylated mismatch-containing 30-mer. Although competition was clearly visible with 50 ng of mismatch-containing DNA, the mismatch-free DNA did not compete until 500 ng, if at all. The far right column on the figure contains no MBP.

The results indicate that, at least with the 30 mers used above, immobilized MBP discriminates between mismatch-containing and perfectly paired DNA with an efficiency of at least three orders of magnitude. Similar results have been obtained using 54 mers with a sequence derived from the V3 loop of HIV. Therefore, even if the discrimination decreases as the amount of perfectly paired duplex increases, the discrimination efficiency when using 300 mers, considered to be the maximum useful length for polymorphism studies of the human genome, should be on the order of a factor of 100.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

---

---

What is claimed is:

1. A method for detecting heterozygosity or the presence of a mutation in heterozygous form in a test DNA sample, wherein said heterozygosity or mutation is the result of a deletion or addition of up to 4 nucleotides, which method comprises:

(a) obtaining a sample of test DNA comprising sequences of all four DNA strands from one or more pairs of chromosomes of a diploid organism;

(b) detectably labeling said test DNA any time prior to step (d) below;

(c) denaturing any double stranded DNA in said sample into single strands and allowing said single strands to reanneal into duplexes;

(d) contacting said detectably labeled DNA duplexes with an immobilized *E. coli* MutS protein or a homologue thereof from a different prokaryotic or eukaryotic species, said protein or homologue being immobilized by direct adsorption to a solid support, and incubating under conditions in which detectably labeled DNA heteroduplexes containing one to four unpaired bases bind to said immobilized protein or homologue; and (e) detecting the binding of any of said heteroduplexes of step (d) to said immobilized protein or homologue, wherein the presence of DNA in the test sample having said deletion or addition results in a detectably labeled DNA heteroduplex bound to the immobilized protein or homologue.

2. A method according to claim 1, wherein said test DNA in said sample is amplified prior to step (b).

3. A method for detecting a homozygous or heterozygous mutation in a test DNA in a sample, wherein said mutation is the result of a deletion or addition of up to about 4 nucleotides, which method comprises:

(a) detectably labeling anytime prior to step (c) below,
  (i) test DNA in said sample, or
  (ii) an added DNA polynucleotide or oligonucleotide as recited in step (b), below, or
  (iii) both (i) and (ii);

(b) denaturing double stranded DNA in said sample into single strands in the presence of an added DNA polynucleotide or oligonucleotide molecule having the wild-type sequence for said mutation, and allowing said strands to reanneal into duplexes;

(c) contacting said detectably labeled polynucleotide duplexes with an immobilized *E. coli* MutS protein, or a homologue thereof from a different prokaryotic or eukaryotic species, said protein or homologue being immobilized by direct adsorption to a solid support, and incubating under conditions in which detectably labeled DNA heteroduplexes containing one to four unpaired bases bind to said immobilized protein or homologue; and (d) detecting the binding of said heteroduplexes of step (c) to said immobilized protein or homologue, wherein the presence of DNA in the test sample having said deletion or addition results in a detectably labeled DNA heteroduplex bound to the immobilized protein or homologue.

4. A method according to claim 3, wherein said test DNA in said sample is amplified prior to step (b).

5. A method according to claim 4, wherein said added DNA polynucleotide or oligonucleotide of step (b) is added prior to said amplifying step.

6. A method according to claim 1 or 3 wherein said immobilized protein or homologue is immobilized to a solid support selected from the group consisting of natural cellulose, modified cellulose, polystyrene, polypropylene, polyethylene, dextran, nylon, polyacrylamide and agarose.

7. A method according to claim 6, wherein said solid support is a nitrocellulose membrane.

8. A method according to claim 1 or 3 wherein said detectably labeled DNA has a detectable label which is a calorimetric compound, a chemiluminescent compound, a bioluminescent compound, a fluorescent compound, biotin or a radiolabel.

9. A method according to claim 8 wherein said detectable label is biotin.

10. A method for detecting heterozygosity or the presence of a mutation in heterozygous form in test DNA in a sample, wherein said heterozygosity or said mutation is the result of a deletion or addition of up to about four nucleotides, which method comprises:

(a) obtaining a sample of test DNA comprising sequences of all four DNA strands from one or more pairs of chromosomes of a diploid organism;

(b) denaturing double stranded DNA in said sample into single strands and allowing said single strands to reanneal into duplexes;

(c) incubating the denatured and reannealed duplexes of step (b) with an *E. coli* MutS protein, or a homologue thereof from a different prokaryotic or eukaryotic species, immobilized by direct adsorption to a solid support, either
  (i) in the presence of a detectably labeled double stranded DNA oligonucleotide capable of binding to said immobilized protein or homologue; or
  (ii) wherein said immobilized protein or homologue was preincubated with and allowed to bind to a detectably labeled double stranded DNA oligonucleotide capable of binding to said immobilized protein or homologue, under conditions in which DNA heteroduplexes containing one to four unpaired bases bind to said immobilized protein or homologue; and (d) detecting the amount of said detectably labeled oligonucleotide bound to said immobilized protein or homologue, wherein the presence of DNA in the test sample having said deletion or addition results in a decrease in detectably labeled DNA heteroduplex bound to the immobilized protein or homologue.

11. A method for detecting a homozygous or heterozygous mutation in test DNA in a sample, wherein said mutation is the result of a deletion or addition of up to about four nucleotides, which method comprises:

(a) denaturing double stranded DNA in said sample into single strands in the presence of an added DNA polynucleotide or oligonucleotide molecule having the wild-type sequence for said mutation, and allowing said single strands to reanneal into duplexes;

(b) incubating the denatured and reannealed duplexes formed in step (a) with an *E. coli* MutS protein, or a homologue thereof from a different prokaryotic or eukaryotic species, immobilized by direct adsorption to a solid support, either
  (i) in the presence of a detectably labeled double stranded DNA oligonucleotide capable of binding to said immobilized protein or homologue; or
  (ii) wherein said immobilized protein or homologue had first been preincubated with, and allowed to bind to, a detectably labeled double stranded DNA oligonucleotide capable of binding to said immobilized protein or homologue prior to said incubating, under conditions in which DNA heteroduplexes containing one to four unpaired bases bind to said immobilized protein or homologue; and (c) detecting the detectably labeled oligonucleotide bound to said immobilized protein or homologue;

wherein the presence of DNA in the test sample having said deletion or addition results in a decrease in detectably labeled DNA heteroduplex bound to the immobilized protein or homologue.

12. A method according to claim 10 or 11, wherein said test DNA in said sample is amplified prior to step (a).

13. A method according to claim 12, wherein said added DNA polynucleotide or oligonucleotide of step (a) is added prior to said amplifying step.

14. A method according to claim 10 or 11, wherein said immobilized protein or homologue is immobilized to a solid support selected from the group consisting of natural cellulose, modified cellulose, polystyrene, polypropylene, polyethylene, dextran, nylon, polyacrylamide and agarose.

15. A method according to claim 14, wherein said solid support is a nitrocellulose membrane.

16. A method for removing from an amplified DNA sample a majority of (i) sequences containing sequence errors introduced during the process of amplification and (ii) minority sequences, wherein said sequence errors and said minority sequences are the result of a deletion or addition of up to 4 nucleotides, which method comprises:

(a) subjecting said amplified DNA sample to conditions of denaturation followed by reannealing, such that said error-containing or said minority sequences form heteroduplexes containing one to four unpaired bases, when paired with error-free sequences or majority sequences respectively, thereby generating in said sample a mixture of perfectly matched duplexes and said heteroduplexes;

(b) contacting the mixture of step (a) with an immobilized *E. coli* MutS protein or a homologue thereof from a different prokaryotic or eukaryotic species said protein or homologue being immobilized by direct adsorption to a solid support, and incubating under conditions in which said heteroduplexes formed in step (a) bind to said immobilized protein or homologue; and (c) removing said immobilized protein or homologue to which said heteroduplexes are bound from said amplified, denatured, and reannealed DNA sample, thereby removing the majority of said sequences containing sequence errors and minority sequences from said amplified DNA sample.

* * * * *

UNITED STATES PATENT AND TRADEMARK OFFICE
CERTIFICATE OF CORRECTION

PATENT NO.     : 6,027,877

DATED          : February 22, 2000

INVENTOR(S)    : Robert E. Wagner, Jr.

It is certified that error appears in the above-identified patent and that said Letters Patent is hereby corrected as shown below:

At column 17, line 63 (in Claim 8), please delete "calorimetric" and substitute therefor -- colorimetric -- .

On the title page, at item [73], please delete "Gene Check, Inc., Vermontville, N.Y." and substitute therefor -- ValiGene Corporation, New York, N.Y. -- .

Signed and Sealed this

Fifteenth Day of May, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:1:

GCACCTGACT CCTGGGGAGA AGTCTGCCGT          30

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:2:

CGTGGACTGA GGACTCCTCT TCAGACGGCA          30

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:3:

CGTGGACTGA GGACCCCTCT TCAGACGGCA          30